US009636360B2

(12) United States Patent
Gurol et al.

(10) Patent No.: US 9,636,360 B2
(45) Date of Patent: May 2, 2017

(54) METHOD AND COMPOSITION FOR TREATING GASTRO-ESOPHAGEAL DISORDERS

(71) Applicant: pH Science Holdings, Inc, Lynnwood, WA (US)

(72) Inventors: Ismail Gurol, Lynnwood, WA (US); Robert Burns, Lynnwood, WA (US); Steven Loyd, Lynnwood, WA (US)

(*) Notice: Subject to any disclaimer, the term of this patent is extended or adjusted under 35 U.S.C. 154(b) by 0 days.

(21) Appl. No.: 14/027,937

(22) Filed: Sep. 16, 2013

(65) Prior Publication Data
US 2014/0079814 A1 Mar. 20, 2014

Related U.S. Application Data

(60) Provisional application No. 61/702,611, filed on Sep. 18, 2012.

(51) Int. Cl.
*A61K 33/10* (2006.01)
*A61K 33/00* (2006.01)
(Continued)

(52) U.S. Cl.
CPC ............... *A61K 33/10* (2013.01); *A61K 9/10* (2013.01); *A61K 9/5047* (2013.01); *A61K 33/00* (2013.01); *A61K 33/08* (2013.01)

(58) Field of Classification Search
None
See application file for complete search history.

(56) References Cited

U.S. PATENT DOCUMENTS 5,681,827 A 10/1997 Field
6,066,342 A 5/2000 Gurol et al.
(Continued)

FOREIGN PATENT DOCUMENTS

GB 2349570 11/2000
WO WO 2005/027939 3/2005
WO WO 2009/073878 6/2009

OTHER PUBLICATIONS

Orlando, Roy C; Esophageal Mucosal Defense Mechanisms; GI Mobility On-Line; May 16, 2006, pp. 1-24 (see http:www.nature.com/gimo/contents/pt1/full/gimo15.html).

(Continued)

*Primary Examiner* — Carlos Azpuru
*Assistant Examiner* — Casey Hagopian
(74) *Attorney, Agent, or Firm* — Dean Craine; Marisa Whitaker

(57) ABSTRACT

An orally administered composition that includes least one alkaline agent with a pH of at least 9.0 to 12.0, mixed in an aqueous vehicle with relatively high surface tension, high viscosity and lateral adhesion properties. When mixed, a low water soluble emulsion is formed that evenly coats and partially adheres to the lower section of the esophagus and the LES and forms a relatively long acting, protective barrier and partially neutralizes gastric acid. In one embodiment, the alkaline agent is potassium hydroxide and the aqueous vehicle is made of hydroxypropyl methyl cellulose, polyethylene glycol or ethylene glycol and additional thickener agents capable of withstanding high pH environments, such as xanthan gum, croscarmellose sodium, and microcrystalline cellulose. Additional organoleptic agents, such as gum Arabic and polyethylene glycol, flavorings, such as sodium chloride, acesulfame potassium, sodium saccharine, and mint, and stabilizers such as colloidal silica made be added.

17 Claims, 3 Drawing Sheets

(51) Int. Cl.
   *A61K 33/08*   (2006.01)
   *A61K 9/10*    (2006.01)
   *A61K 9/50*    (2006.01)

(56) References Cited

U.S. PATENT DOCUMENTS

| | | |
|---|---|---|
| 6,395,307 B1 | 5/2002 | Banning et al. |
| 7,901,717 B1* | 3/2011 | Falkenberg .......... A61K 9/0095 424/754 |
| 2002/0009478 A1 | 1/2002 | Dobrozsi |
| 2003/0175360 A1* | 9/2003 | Luzzatti ................ A61K 31/00 424/653 |
| 2006/0183776 A9* | 8/2006 | Pratt .................... A61K 31/445 514/319 |
| 2007/0218126 A1* | 9/2007 | Gurol et al. .................. 424/458 |
| 2012/0107414 A1 | 5/2012 | Lipp et al. |

OTHER PUBLICATIONS

European Search Report, PC-EP-21076268; Application No. 13838573.7 (PCT US2013/0670322; pp. 1-9.

\* cited by examiner

Table 4

| | | | |
|---|---|---|---|
| P. gingivalis | 9.5 | 5.6 | 41% |
| Campylobacter sp. | 12.6 | 7.8 | 38% |
| Eubacterium sp. | 4.2 | 4.4 | 5% |
| Fusobacterium sp. | 10.5 | 8.9 | 15% |
| P. micros | 0 | 4.4 | |
| Beta hemolytic streptococci | 9.5 | 0 | 100% |
| Eikenella corrodens | 5.3 | 0 | 100% |

*FIG. 4*

METHOD AND COMPOSITION FOR TREATING GASTRO-ESOPHAGEAL DISORDERS

This utility patent application is based upon and claims the filing date benefit of U.S. provisional patent application (Application No. 61/702611) filed on Sep. 18, 2012.

BACKGROUND OF THE INVENTION

1. Field of the Invention

This invention relates to methods and compositions for treating various gastro-esophageal disorders including esophagitis, gastro-esophageal reflux disease ('GERD'), laryngopharyngeal reflux ('LPR'), esophageal ulcers, synchronous diaphragmatic flutter ('SDF'), inadequate lower esophageal sphincter ('LES') function, and reducing esophageal infection and dysphagia due to cancer treatment side-effects.

2. Description of the Related Art

Gastro-esophageal reflux disease (hereinafter referred to as 'GERD') is a chronic symptom caused by stomach acid coming up through the lower esophageal sphincter and into the esophagus. Laryngopharyngeal reflux, (hereinafter referred to as 'LPR'), is a chronic symptom caused by stomach acid coming up through the esophagus and the upper esophageal sphincter and into the larynx and nasal airway. The underlying cause of esophagitis, esophageal ulcers, and GERD is normally the inadequate closure of the lower esophageal sphincter, (hereinafter known as LES) and can also be caused or exacerbated by medical procedures such as endoscopic examinations of the esophagus and intubation of the gastro-esophageal tract. The underlying cause of LRP is normally the inadequate closure of the LES and the upper esophageal sphincter (hereinafter known as UES).

GERD and LPR sometimes cause injury to the esophagus which may include: (1) reflux esophagitis (necrosis of esophageal epithelium causing ulcers near the junction of the stomach and esophagus or LES); (2) esophageal strictures (persistent narrowing of the esophagus caused by inflammation; and (3) Barrett's esophagus (changes in the epithelial cells of the esophagus from squamous to intestinal columnar epithelium); (4) esophageal ulcers; and even (5) esophageal adenocarcinoma (cancer), and (6) synchronous diaphragmatic flutter ('SDF'). Endoscopic examination of the esophagus and intubation of the gastro-esophageal tract, especially if pre-existing esophageal injury is present, might cause and exacerbate those injuries.

One treatment for GERD and LPR involves the use of proton pump inhibitors ("PPIs") that reduce stomach acid production. PPIs are widely used, and many patients are dependent on them. In 2010 and 2011, the U.S. Food and Drug Administration (hereinafter referred to as 'FDA') issued warning letters regarding the long term use of PPIs and many patients are fearful that their GERD and LRP symptoms will return if PPIs are discontinued.

SUMMARY OF THE INVENTION

It is an object of the present invention to provide a composition and alternative method for treating esophagitis, esophageal strictures, Barrett's esophagus, synchronous diaphragmatic flutter, esophageal ulcers, inflammation, and associated bacterial growth in the esophagus, GERD and LRP due to LES insufficiency or injury due to medical procedures, and improve esophageal function that has deteriorated due to cancer treatment side-effects. The method includes the use of an alkaline composition made of a sticky, highly viscous, emulsion that temporarily coats the esophageal mucosa tissue, heals inflamed esophageal tissue, reduces esophageal pain associated with inflammation and injury to the esophagus, reduces disease-causing bacteria, and also acts to neutralize the natural gastric juices in the esophagus and around the LES. The alkaline composition is formulated to coat and reside in the esophagus and around the LES a sufficient amount of time to reduce pain, reduce inflammation, improve the function of the esophageal epithelial tissue and mucosa, and improve the function of the lower esophageal sphincter ("LES"). A typical dose is 5 ml to 15 ml of the alkaline composition one to three times a day depending on the severity of the esophageal injury.

More specifically, the alkaline composition includes least one alkaline agent with a pH of at least 9.0 to 12.0, mixed in an aqueous vehicle with relatively high surface tension, high viscosity and lateral adhesion properties. When mixed, a low water soluble emulsion is formed that evenly coats and partially adheres to the lower section of the esophagus and the LES and forms a relatively long acting, protective barrier and partially neutralizes gastric acid. In one embodiment, the alkaline agent is potassium hydroxide and the aqueous vehicle is made of hydroxypropyl methyl cellulose, polyethylene glycol or ethylene glycol and additional thickener agents capable of withstanding high pH environments, such as xanthan gum, croscarmellose sodium, and microcrystalline cellulose. Additional organoleptic agents, such as gum Arabic and polyethylene glycol, flavorings, such as sodium chloride, acesulfame potassium, sodium saccharine, and mint, and stabilizers such as colloidal silica may be added.

To improve adhesion to the surround tissues, the alkaline composition may also include other ingredients that are chemically compatible in higher pH environments that act as thickening agents, such as xanthan gum, and microcrystalline cellulose, croscarmellose sodium, or as organoleptic agents, such as gum Arabic and polyethylene glycol derivatives.

DESCRIPTION OF THE DRAWINGS

FIG. 4 is a table showing the bacterial count results conducted in Study 1.

DESCRIPTION OF THE PREFERRED EMBODIMENT(S)

Figure 1:
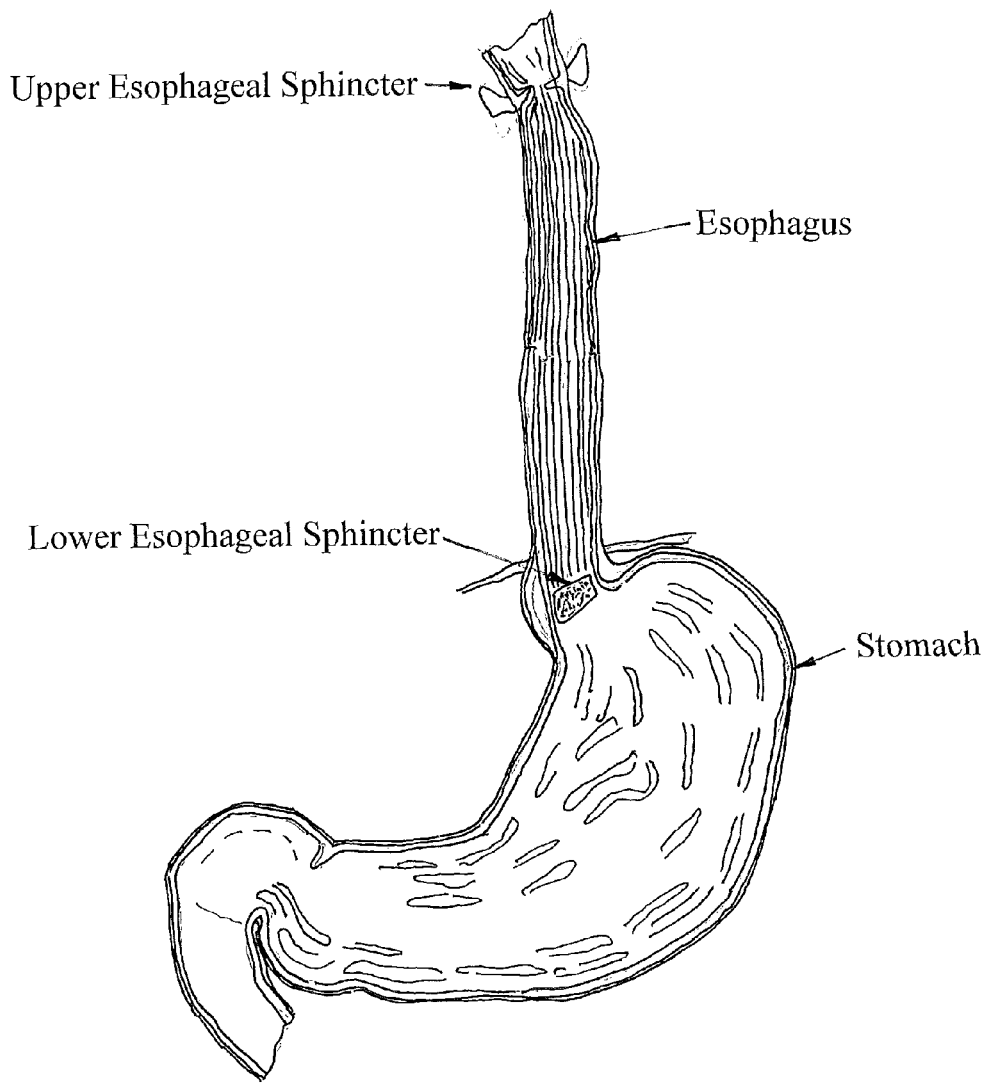
FIG. 1 is an illustration of a patient's esophagus, stomach, the UES and the LES.
Figure 2:
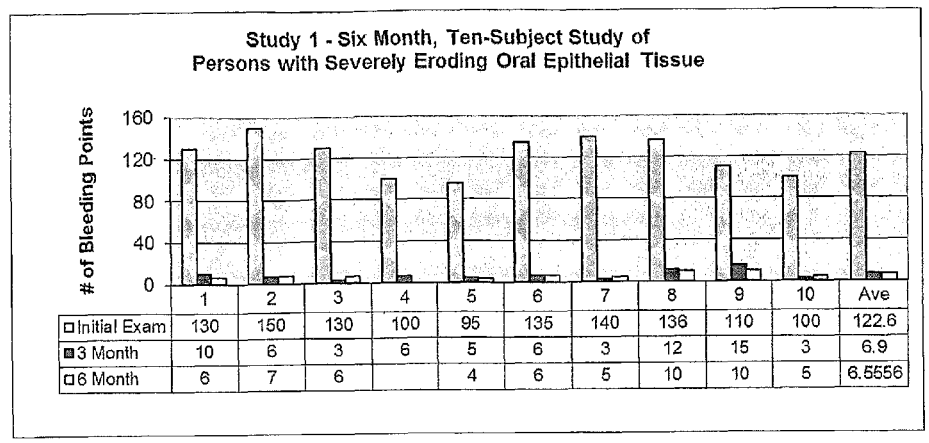
FIG. 2 is a table showing the anti-inflammatory and healing results from Study 1.
Figure 3:
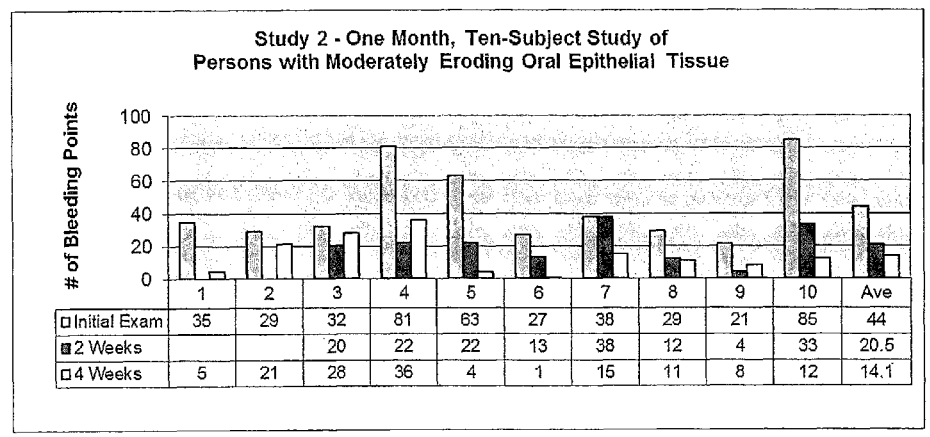
FIG. 3 is a table showing the anti-inflammatory and healing results of Study 2.

The present invention provides a method and an alkaline composition used to prevent and ameliorate pain, inflammation, bacteria colonization, and irritation to the esophagus and more serious conditions related to gastro-esophageal reflux disease ("GERD"), laryngopharyngeal reflux ("LPR"), and poor function of the lower esophageal sphincter ("LES") in adults and infants and conditions related to GERD, LPR, and LES and certain damaging side-effects in the esophagus associated with cancer treatments.

The alkaline composition is orally administered and includes least one alkaline agent with a pH of at least 9.0 to 12.0, mixed in an aqueous vehicle with relatively high surface tension, high viscosity and relatively high, lateral adhesion properties. When mixed, the alkaline composition forms an emulsion that when administered orally evenly coats and partially adheres to the lower section of the esophagus and the LES. The alkaline composition forms a relatively long acting, protective barrier that also partially neutralizes gastric acid.

In one embodiment, the alkaline agent is potassium hydroxide and the aqueous vehicle is made of hydroxypropyl methyl cellulose, polyethylene glycol or ethylene glycol and additional thickener agents capable of withstanding high pH environments, such as xanthan gum, croscarmellose sodium, and microcrystalline cellulose. Additional organoleptic agents, such as gum Arabic and polyethylene glycol, flavorings, such as sodium chloride, acesulfame potassium, sodium saccharine, and mint, and stabilizers such as colloidal silica may be added.

The composition preferably includes potassium hydroxide, a strong alkaline agent that is capable of achieving the desired pH for the composition, retaining a high pH upon introduction to the esophagus. Significantly, the composition of the present preferred embodiment and having a pH of 9.5 to 11.5 will, after dilution in the esophagus, provide a resulting pH of at least 9.0 in the esophagus without any negative reaction to the tissue in the esophagus. In an aqueous composition, potassium hydroxide is at 0.25% to 6.0% by weight, and preferably 1.0% to 5.0% by weight. In addition to potassium hydroxide, the composition preferably includes additional alkaline agents, preferably aluminum hydroxide, calcium carbonate, magnesium carbonate, and magnesium hydroxide.

Alkaline substances having long-lasting activity include alkali and alkaline earth metal hydroxides, such as sodium and potassium hydroxide, calcium carbonate and magnesium hydroxide, are suitable for use in the present invention. The rapid "antacid effect" (referring to the ability of a substance to neutralize and/or to buffer an acid) of stronger alkaline substances such as alkali and alkaline earth metal hydroxides is also used in the present invention. Alkali metal hydroxides suitable for use in the present invention include sodium hydroxide and potassium hydroxide, or a transition metal hydroxide, such as aluminum hydroxide, with potassium hydroxide being preferred for the present invention.

The preferred embodiment of the present invention includes potassium hydroxide for rapid antacid effects and one or more, and preferably all, of aluminum hydroxide, calcium carbonate, and magnesium carbonate for residual acid reduction.

There are two methods for manufacturing the composition. The first method requires the production of granules made of calcium carbonate, magnesium hydroxide, and potassium hydroxide which are coated with croscarmelose sodium and microcrystalline cellulose in 20-30% water. The granules are then dried to 3-10% water. The above steps are discussed in U.S. Pat. No. 6,066,342, which is now incorporated by reference. Additional thickening agents, water and organoleptic agents may be added.

Using the second method, the granulation step above is eliminated and the ingredients are mixed together in an aqueous solution and then used to make the emulsion.

The alkaline composition is partially dissolved in water, and a thickening agent is added that increases the composition's viscosity, increases shelf life, and provides protection in a high pH environment. Suitable thickeners include xanthan gum, croscarmellose sodium (i.e. cellulose gum) and microcrystalline cellulose (i.e cellulose gel), which will withstand pH environments of up to 12.0 without substantial degradation. The composition of the present invention may alternately be compounded as a liquid suspension; however a more viscous gel or emulsion is preferred for application and coating of the esophagus. A stabilizing suspension agent such as colloidal silica may also be used.

In addition to alkaline agents and thickeners, the composition may also include inactive excipients such as organoleptic agents, such as gum arabic and polyethylene glycol, for feel in the oral cavity and upper esophagus or flavoring agents such as sodium chloride, acesulfame-potassium, sodium-saccharine, and mint.

In each embodiment of the composition presented herein, the composition has the following physical properties: pH: 9.0 to 11.5

Specific Gravity: 1.05 to 1.15 gm/cc

Viscosity: 6,000 to 29,000 cP using small sample adapter and SC4-21/13R spindle on Brookfield DV2TRV Viscometer Lateral Adhesion/Stickiness: $10^{-2}$ to $10^{-6}$ Newtons When formulated into an emulsion, the alkaline composition is stable for a period in excess of one year when stored at ambient conditions, and without significant degradation of the viscosity, lateral adhesion or "stickiness" of the emulsion despite the highly alkaline environment. Lateral adhesion allows the emulsion to coat the esophageal mucosa uniformly at it flows down the esophagus. It should be understood that composition may be reformatted into a suspension, gel or paste-like substance.

The following studies were performed to demonstrate columnar epithelium tissue healing characteristics of the composition:

Study 1

In this study, ten patients with severely eroding and inflamed oral epithelial tissue were tested. A standardized test was used to establish a baseline number of bleeding points in the oral cavity. A photograph was also taken of the epithelial tissue and a bacterial sample was taken. The preferred embodiment of the composition was applied daily by each patient for 90 days. The patients then returned for examination. The average number of bleeding points was reduced from 123 to 7 after 90 days.

"Before" and "after" pictures taken of each patient indicated the epithelial tissue had returned to normal, healthy pinkish white color and the inflammation had abated after application of the emulsion. Bacteria counts of selected pathogenic bacteria were substantially reduced. All subjects reported an immediate reduction in tissue pain and irritation upon applying the composition. The study concluded after 180 days.

Study 2

In this study, ten patients with moderately eroding oral epithelial tissue were examined Again, a standard test established a baseline number of bleeding points in the oral cavity. The preferred embodiment of the composition as applied daily for 14 days. The patients then returned for examination. The average number of bleeding points was reduced from 44 to 20 in two weeks.

Study 3

In this study, the University Of Washington School Of Dentistry participated that conducted a double-blind, placebo-controlled, small-n format. Researchers recruited patients with moderately eroding oral epithelial tissue. Daily application of the composition resulted in significant improvement in the epithelial tissue health within two weeks.

Daily application of the preferred embodiment of the invention was associated with measurable improvement in the function of stratified squamous epithelial tissue.

The only contra-indication for the Company's emulsion is due to the presence of calcium which reduces tetracycline antibiotic absorption if both are taken at the same time. Tetracycline is a broad spectrum antibiotic that has been supplanted by several new antibiotics.

In compliance with the statute, the invention described herein has been described in language more or less specific as to structural features. It should be understood, however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

We claim:

1. A method of reducing or treating damage to the esophagus and the lower esophageal sphincter caused by physical trauma or gastric acid, comprising the administrating to a patient in need thereof an oral composition in the form of an emulsion consisting of:
   an alkali metal hydroxide 0.25% to 6.0% by weight, a thickening agent, and an organoleptic agent mixed in water that produces a pH between 9.0 to 12.0 and a specific gravity value from 1.05 to 1.15 gm/ml, a viscosity value between 6000 to 29,000 cP, and a lateral adhesion value between $10^{-2}$ to $10^{-6}$ Newtons, said organoleptic agent selected from the group consisting of: hydroxypropyl methyl cellulose, polyethylene glycol or ethylene glycol;
   an optional alkaline agent;
   an optional stabilizing suspending agent; and,
   an optional flavoring agent.

2. The method as recited in claim 1, wherein said alkali metal hydroxide is potassium hydroxide.

3. The method as recited in claim 1, wherein said thickening agent selected from the group consisting of: xanthan gum, croscarmellose sodium, and microcrystalline cellulose.

4. The method as recited in claim 1, wherein said alkali metal hydroxide is sodium hydroxide.

5. The method as recited in claim 2, wherein said alkaline agent selected from the group consisting of: aluminum hydroxide, calcium carbonate, magnesium hydroxide, and magnesium carbonate.

6. The method as recited in claim 3, wherein said composition includes calcium carbonate 8% to 22% by weight and magnesium hydroxide 0.1% to 3.0% by weight.

7. The method as recited in claim 1, wherein said alkaline agent selected from the group consisting of: aluminum hydroxide, calcium carbonate, magnesium hydroxide, and magnesium carbonate.

8. The method as recited in claim 3, wherein said alkaline agent selected from the group consisting of: aluminum hydroxide, calcium carbonate, magnesium hydroxide, magnesium carbonate, and mixtures thereof.

9. The method as recited in claim 1, wherein said composition includes calcium carbonate 8% to 22% by weight and magnesium hydroxide 0.1% to 3.0% by weight.

10. The method as recited in claim 2, wherein said thickening agent selected from the group consisting of: xanthan gum, croscarmellose sodium, and microcrystalline cellulose.

11. The method as recited in claim 10, wherein said alkaline agent selected from the group consisting of: aluminum hydroxide, calcium carbonate, magnesium hydroxide, and magnesium carbonate.

12. The method as recited in claim 1, wherein said stabilizing suspending agent is colloidal silica.

13. The method as recited in claim 1, wherein said flavoring agent selected from the group consisting of: sodium chloride, acesulfame-potassium, sodium-saccharine and mint.

14. An oral composition for reducing or treating tissue damage to lower or upper esophageal sphincters or to the esophagus caused by physical trauma, inflammation or gastric acid, consisting of:
   a. 0.25% to 6.0% by weight of an alkali metal hydroxide with a pH of at least 9.0 to 12.0 mixed in water;
   b. a thickening agent stable in a pH 9.0 or greater selected from the group consisting of: xanthan gum, croscarmellose sodium, or microcrystalline cellulose;
   c. an organoleptic agent selected from the group consisting of: hydroxypropyl methyl cellulose, polyethylene glycol or ethylene glycol;
   d. a sufficient volume of alkali metal hydroxide, water, thickening agent and organoleptic agent to make an emulsion with a pH value between 9.0 to 11.5, a specific gravity from 1.05 to 1.15 gm/ml; a viscosity from 6000 to 29,000 cP, and a lateral adhesion value from $10^{-2}$ to $10^{-6}$ Newtons;
   e. an optional alkaline agent;
   f. an optional stabilizing suspending agent; and,
   g. an optional flavoring agent.

15. The composition as recited in claim 14, wherein said alkaline agent selected from the group consisting of: aluminum hydroxide, calcium carbonate, magnesium hydroxide, and magnesium carbonate.

16. The composition as recited in claim 14, wherein said stabilizing suspending agent is colloidal silica.

17. The composition as recited in claim 14, wherein said flavoring agent selected from the group consisting of: sodium chloride, acesulfame-potassium, sodium-saccharine and mint.

* * * * *